United States Patent [19]

Petrini et al.

[11] 4,412,177

[45] Oct. 25, 1983

[54] EDDY CURRENT INSPECTION TOOL WHICH IS SELECTIVELY OPERABLE IN A DISCONTINUITY DETECTION MODE AND A DISCONTINUITY MAGNITUDE MODE

[75] Inventors: Richard R. Petrini; Dorin F. Van Lue, both of Livermore, Calif.

[73] Assignee: The United States of America as represented by the U.S. Department of Energy, Washington, D.C.

[21] Appl. No.: 201,946

[22] Filed: Oct. 29, 1980

[51] Int. Cl.³ .................... G01N 27/90; G01R 33/12; G01B 7/14; G02B 5/17

[52] U.S. Cl. .................... 324/226; 324/207; 324/219; 324/227; 324/238; 350/96.26

[58] Field of Search ............... 324/207, 208, 219–221, 324/226, 227, 234, 236–240, 327, 329; 350/96.26

[56] References Cited

U.S. PATENT DOCUMENTS

| | | | |
|---|---|---|---|
| 3,185,923 | 5/1965 | Sadofsky | 324/226 |
| 3,723,861 | 3/1973 | Samples | 324/237 |
| 3,941,121 | 3/1976 | Olinger et al. | 350/96.26 X |
| 4,139,822 | 2/1979 | Urich et al. | 324/219 |
| 4,268,791 | 5/1981 | Rogel et al. | 324/219 X |
| 4,274,054 | 6/1981 | Savidge et al. | 324/237 X |
| 4,303,879 | 12/1981 | Podhrasky | 324/329 |
| 4,309,658 | 1/1982 | Leff | 324/327 |

OTHER PUBLICATIONS

Eddy Current Test Equipment "Nondestructive Testing Handbook" Robt. C. McMaster, vol. II N.Y., The Ronald Press Co., 1959 Sec 40, pp. 1–10.

Lancaster, Donald E., Electronic Metal Locators.

*Primary Examiner*—Gerard R. Strecker
*Attorney, Agent, or Firm*—Marvin J. Marnock; William H. F. Howard; Richard G. Besha

[57] ABSTRACT

A miniaturized inspection tool, for testing and inspection of metal objects in locations with difficult accessibility, which comprises eddy current sensing equipment (12) with a probe coil (11), and associated coaxial coil cable (13), coil energizing means (21), and circuit means (21, 12) responsive to impedance changes in the coil as effected by induced eddy currents in a test object to produce a data output signal proportional to such changes. The coil and cable are slideably received in the utility channel of the flexible insertion tube 17 of fiber-optic scope 10. The scope 10 is provided with light transmitting and receiving fiberoptics for viewing through the flexible tube, and articulation means (19, 20) for articulating the distal end of the tube and permitting close control of coil placement relative to a test object. The eddy current sensing equipment includes a tone generator 30 for generating audibly signals responsive to the data output signal. In one selected mode of operation, the tone generator responsive to the output signal above a selected level generates a constant single frequency tone for signalling detection of a discontinuity and, in a second selected mode, generates a tone whose frequency is proportional to the difference between the output signal and a predetermined selected threshold level.

3 Claims, 5 Drawing Figures

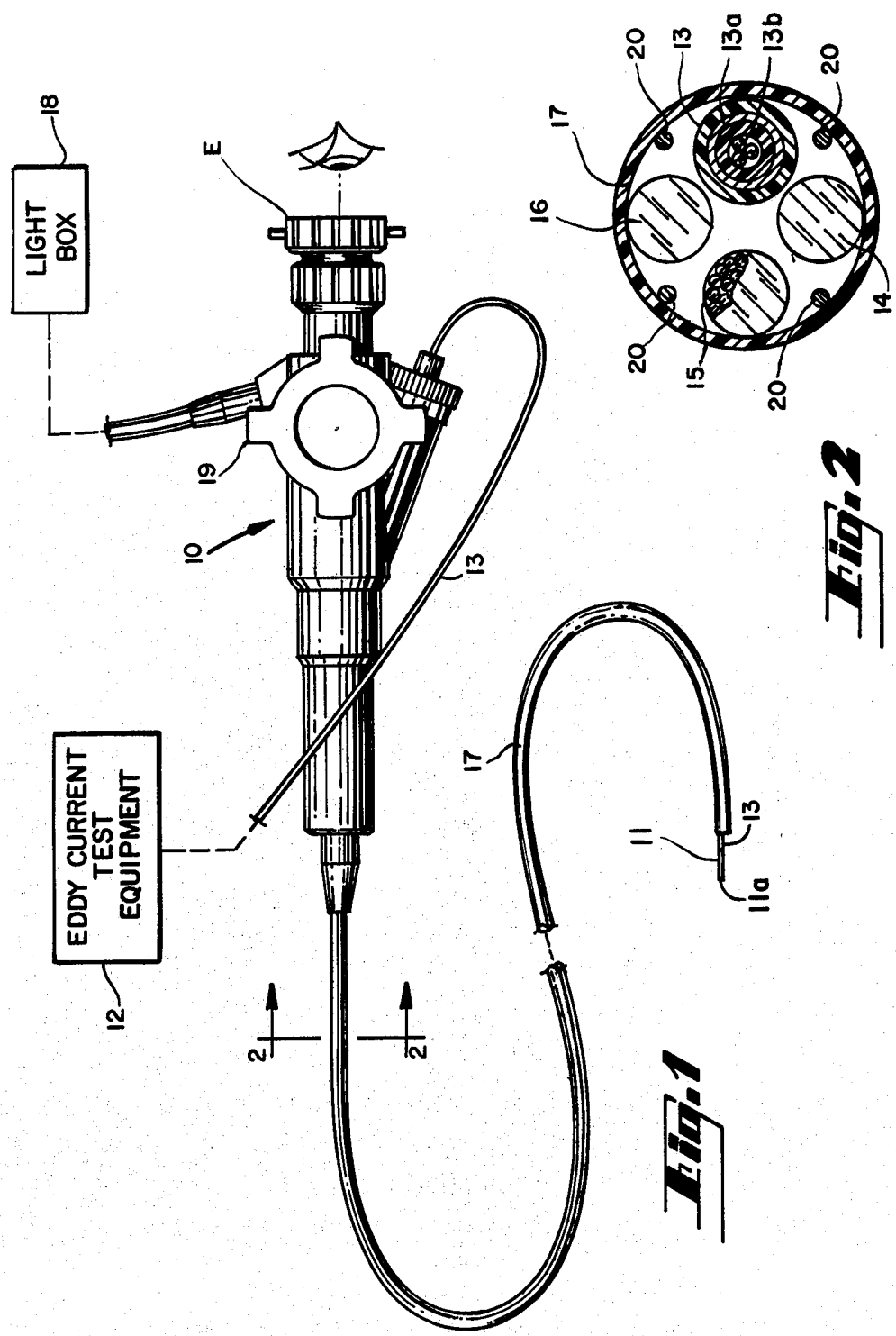

EDDY CURRENT INSPECTION TOOL WHICH IS SELECTIVELY OPERABLE IN A DISCONTINUITY DETECTION MODE AND A DISCONTINUITY MAGNITUDE MODE

The U.S. Government has rights in this invention pursuant to Contract W-7405-ENG-48 between the U.S. Department of Energy and the University of California.

BACKGROUND OF THE INVENTION

The invention relates to inductive displacement measuring systems and, more particularly, to an inspection tool which permits simultaneous visual and eddy current inspection of objects in locations for which there is difficult access; and provides an audible signal for indicating the detection and magnitude of discontinuities therein, such as, cracks, seams, or inclusions, or the degree of object displacement.

Eddy current testing utilizes the application of inductive techniques, the basic principles of which are well known. In practice, a probe coil carrying an alternating current generates a pulsating magnetic field, and when the coil is placed a nominal distance from the metal test object so that the test object is located within the pulsating magnetic field, current flow is induced within and on the surface of the test object. The induced currents, called "eddy currents" because of the circular pattern, produce a secondary a.c. magnetic field that opposes and reduces the intensity of the coil's magnetic field. Changes in the impedance of the exiting coil can then be analyzed for inspection purposes.

The classic application is in nondestructive testing. A typical procedure for such testing involves placement of the probe coil adjacent to the flat surface of a metallic test object. The influence of several physical properties of the test specimen upon the impedance characteristics of the probe coil can then be calculated for various test frequencies. With appropriate selection of an operating frequency, as determined by theory or by experiment, the depth of eddy current penetration is controlled to "look" at the surface only or into the metal itself to locate discontinuities which upset the current flow, such as cracks, or inclusions. From the impedance change it is often possible to measure, quantitatively and independently of each other, such parameters as the conductivity, dimensions, and magnetic permeability of the test object, as well as such features as the magnitude and direction of cracks, seams, inclusions, or the like.

The development of eddy current test equipment has led to numerous designs to eddy current test equipment in which test coils are connected to the electronic test instruments in a variety of measurement effects. For example, in a typical circuit as disclosed in the text "Nondestructive Testing Handbook" (edited for the Society for Nondestructive Testing, by Robert C. McMaster, Vol. II, N.Y., The Ronald Press Co., 1959, Sec. 40, pp 1-10) the sensing coil is normally a section or leg of a balanced bridge network. As a metal object moves toward the coil, or vice versa, more eddy currents are generated in the object material and losses within the bridge network increase. As the object (or coil) moves away, the losses decrease. These unbalanced conditions, produce by the impedance changes in the test coil, are sensed and converted into a signal which is directly proportional to the distance between the coil and test object.

However, irrespective of the particular form of circuit chosen, it has therefore been especially difficult to apply eddy current test methods in locations where accessibility is difficult; as, for example, small diameter bores, cylinders, and the like. In such applications, positioning of the coil relative to the test object is either impossible due to the relatively large size of the test coil and associated equipment or, at best, becomes mere guesswork. Furthermore, observing meter readings while at the same time carefully controlling the movement of the coil over the surface of the test object is very difficult, if not impossible.

Accordingly, it is an object of the invention to provide a miniature eddy current inspection tool which allows for simultaneous visual and eddy current testing of an object in relatively inaccessible locations.

It is another object to provide an eddy current inspection tool which provides an audible signal for indicating detection and magnitude of discontinuities, such as cracks, seams, or inclusions, in the test object.

It is a further object to provide a miniaturized inspection tool for the simultaneous visual and eddy current testing of objects in locations with difficult accessibility, and which can provide a first audible signal indicating detection of a discontinuity, such as a coating interface, crack, seam, or inclusion, in the test object, and a second audible signal which is frequency-dependent upon the magnitude and direction of the discontinuity or the degree of object displacement. It is still a further object to provide a miniaturized inspection tool comprising an eddy current sensor and a fiberoptic scope for visual and eddy current testing of objects in remote or difficulty accessible locations, and which is selectively operable in a first mode to provide a constant single frequency signal for signalling the detection of a discontinuity, or which can be operated in a second mode for generating a tone whose frequency is proportional to the difference between the sensor signal and a given threshold level as an indication of object displacement or the magnitude and direction of a discontinuity, such as a crack, seam, interface, or inclusion.

Additional objects, advantages, and novel features of the invention, will be set forth in part of the description which follows and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

The present invention is a miniature inspection tool which is suitable for conducting eddy current inspection of objects in remote or nearly inacccessible locations. The tool comprises an eddy current sensor assembly and a fiberoptic scope. The sensor coil and its attached coaxial cable are of substantially equal diameter and of a size small enough to fit the utility channel of a fiberoptic scope, such as a fiberoptic medical scope.

It is therefore possible to view the surface of the test and the positioning of the probe coil relative as the coil is selectively moved by articulation control means provided on the scope. The apparatus includes automatic indicating means which is responsive to the sensor output signal and is selectively operable in a first mode for generating a constant single frequency tone upon detection of a discontinuity whenever the output signal exceeds a given threshold level, or can be operated in a second mode for generating a tone whose frequency is proportional to the difference between the transducer output signal and the given threshold level, and is indicative of the degree of displacement of the object or the magnitude and direction of discontinuities in the object.

BRIEF DESCRIPTION OF THE DRAWING

The accompanying drawings, which are incorporated in and form a part of the specification, illustrate a preferred embodiment of the present invention, and, together with the description serve to explain the principles of the invention. In the drawings:

FIG. 1 shows the general form of the apparatus of the invention as it appears in use;

FIG. 2 is an enlarged cross-sectional view through the flexible cable which carries the eddy current sensor coil cable and the fiberoptic cables of the scope as taken along the line 2—2 of FIG. 1 and illustrating a typical arrangement wherein the coaxial coil cable extends through the utility channel of a fiberoptic scope;

DESCRIPTION OF A PREFERRED EMBODIMENT

Figure 3:
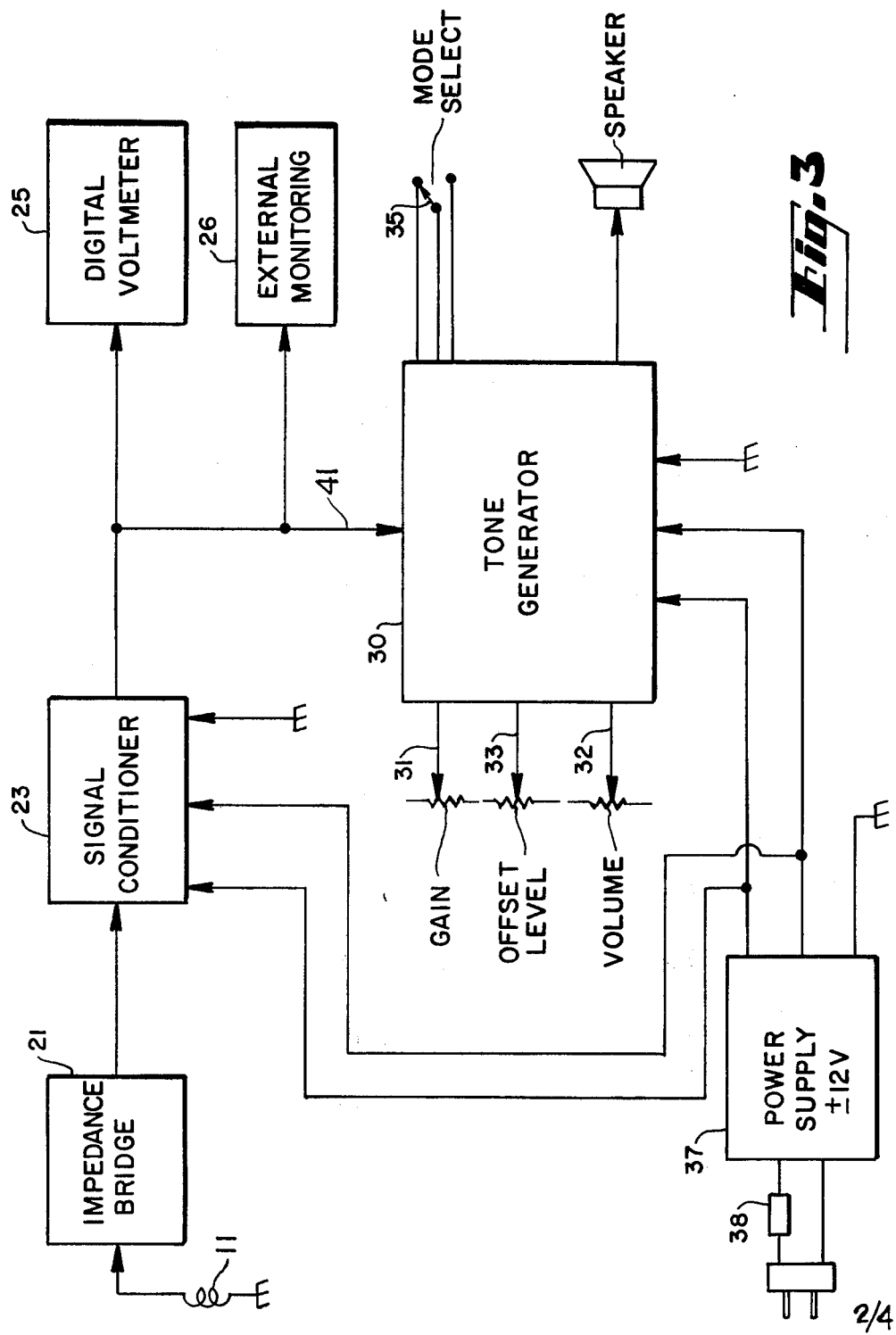
FIG. 3 is a block diagram which shows the eddy current sensor assembly of the invention.

Referring more particularly to the drawings, there is shown in FIG. 1 a typical arrangement of the invention as it would appear in use. The eddy current test equipment is preferably of the type which relies on impedance variations of the test coil for providing information about the object to be inspected. The coil 11 is installed as one leg of a bridge circuit, which conventionally is activated with a high frequency signal generated by an oscillator connected diagonally across the bridge to two of the junctions between the legs with the bridge output taken from the other two junctions. Changes in the coil impedance, when effected by the magnetic fields produced by eddy currents in the target object, produce an unbalance in the bridge circuit and a resulting output signal from the bridge. This output signal is conditioned and converted to an analog signal directly proportional to the target object displacement or to the magnitude and distance of a discontinuity.

Aside from the miniaturized test coil, this portion of the eddy current sensor equipment is conventional and commercially available. For convenience purposes it is packaged in a housing 12 with the coil cable 13 attached thereto. The test coil 11 (also often referred to as a probe coil 11), which terminates at tip 11a, is manufactured with a very small diameter which is slightly smaller than the cable 13 to which it is attached. The cable diameter—for example, 75 mils—is of such size that the coil and cable fit easily through the utility channel of a fiberoptic scope 10 which may be a conventional medical or industrial fiberoptic scope.

As shown in FIG. 2, the coaxial coil cable 13 comprising an outer shield conductor 13a and a coaxial center conductor 13b and the fiberoptic cables 14, 15, 16 of the scope are carried within the flexible insertion tube 17 which serves as a cable housing. The fiberoptic cables 14, 16 are coupled to a light source 18 for transmitting light for illumination of the test object. A suitable light source is a Halogen-type lamp, Model RH-150A3, available from Machida America, Inc.

The cable 15 is a fiberoptic cable which returns reflected light from the target object, conventionally through light-gathering lenses at the distal end of the scope of the eyepiece E. The fiberoptic scope, of conventional type such as a Machida America, Inc. fiberscope Model FBA-11-160, includes articulation controls 19 for articulating the distal end of the flexible insertion tube and the probe coil extending from the distal end in both right-and-left and up-and-down directions. The articulation means includes control cables 20 affixed to the inner wall of the tube 17 in equispaced relation with the coil cable 13 extended through the utility channel of the scope, and being slideably received therein the probe coil cable can be longitudinally adjusted relative to the tube for controlling the displacement of the coil with respect to a test object. The fiberoptic illumination greatly facilitates this procedure.

The probe coil which, in typical fashion, is electrically connected at the distal end of the coaxial cable 13 with its coils coaxial with the center line of the conductor 13b, is encapsulated in a nonconductive material, typically an epoxy compound, the thickness of which is the limiting factor in controlling the operating gap between the coil and target object for the inductive system. A gap in the range equal to the radius of the sensing coil or one-half or less of the radius is feasible for most applications.

An operating frequency for the eddy current test equipment is selected, as determined by theory or experimentation, to provide most sensitivity. The transducer output signal, however, is affected by a number of factors, such as resistivity and permeability of the target material, which have a bearing in the calibration of the output signal for providing useful information providing the test object.

A unique feature of the subject invention is its capability of audibly signalling when a discontinuity, such as crack, seam, interface, or the like, is located. It can be operated to provide a single frequency tone for purposes such as signalling detection and location of a discontinuity, and it can also be operated in an alternative mode wherein a tone is generated with a frequency proportional to the difference between the transducer output signal and a given threshold level. The operator, listening to the variations in tone while observing placement of the probe coil with respect to the test object, can therefore obtain useful information with respect to the test object without the need for having to repeatedly look at a signal display, such as a voltmeter or oscilloscope.

The test coil 11 and associated eddy current sensor assembly of the invention is shown in the block diagram of FIG. 3. It comprises the probe coil 11 which is electrically coupled to an impedance bridge 21. In conventional manner, the bridge output which is controlled by impedance changes in the coil 11 is conditioned by a signal conditioner 23 which detects and converts the bridge output to an analog signal. A Displacement Measuring System, Model KD-2310, available from the Kaman Sciences Corporation, is representative. This analog signal constitutes the transducer data output signal which includes information about the target object. As is conventional, the data output signal is coupled to a digital voltmeter 25 for voltage readout and to an output terminal 26 where it can be selectively coupled to other display means, such as an oscilloscope or recorder for external monitoring or to a computer interface for data processing.

In the instant invention, the transducer data output signal is coupled to a tone generator 30 which is provided with gain and volume controls 31, 32 and an offset level control (threshold level) 33. The volume control adjusts the audio output level, and the offset level control selects the input level or threshold voltage above which the tone generator will generate a tone. If the transducer output signal which is input to the generator is less than the threshold level, no tone is produced.

In addition, the tone generator is provided with a mode select switch 35 which selects a mode of operation for the tone generator. In a first mode, called a "chirp" mode, a constant tone is generated when the input signal to the tone generator exceeds the threshold level. It thus indicates the detection of a discontinuity in nondestructive test applications or the displacement of the target object beyond a predetermined amount when used in displacement applications. If the probe coil is moved in fast transitions back and forth across a crack in the object surface, a "chirping" sound is produced.

In a second mode of operation, a "feedback scan mode" selected by moving the switch 35 to its other contact, a tone is generated only if the threshold level is exceeded. It differs from the first mode, however, in that the frequency of the generated tone is proportional to the difference between the input signal and the threshold level when the input signal exceeds the threshold. Characteristically, it is such that the larger the difference between input signal and threshold the higher is the frequency.

For powering the equipment, an a.c. power supply 37 is provided which can supply 12 volts alternating current of the signal conditioner and tone generator. It is adapted to be plugged into a 115 volt a.c. outlet and is provided with an ON/OFF switch 38.

Figure 4A:
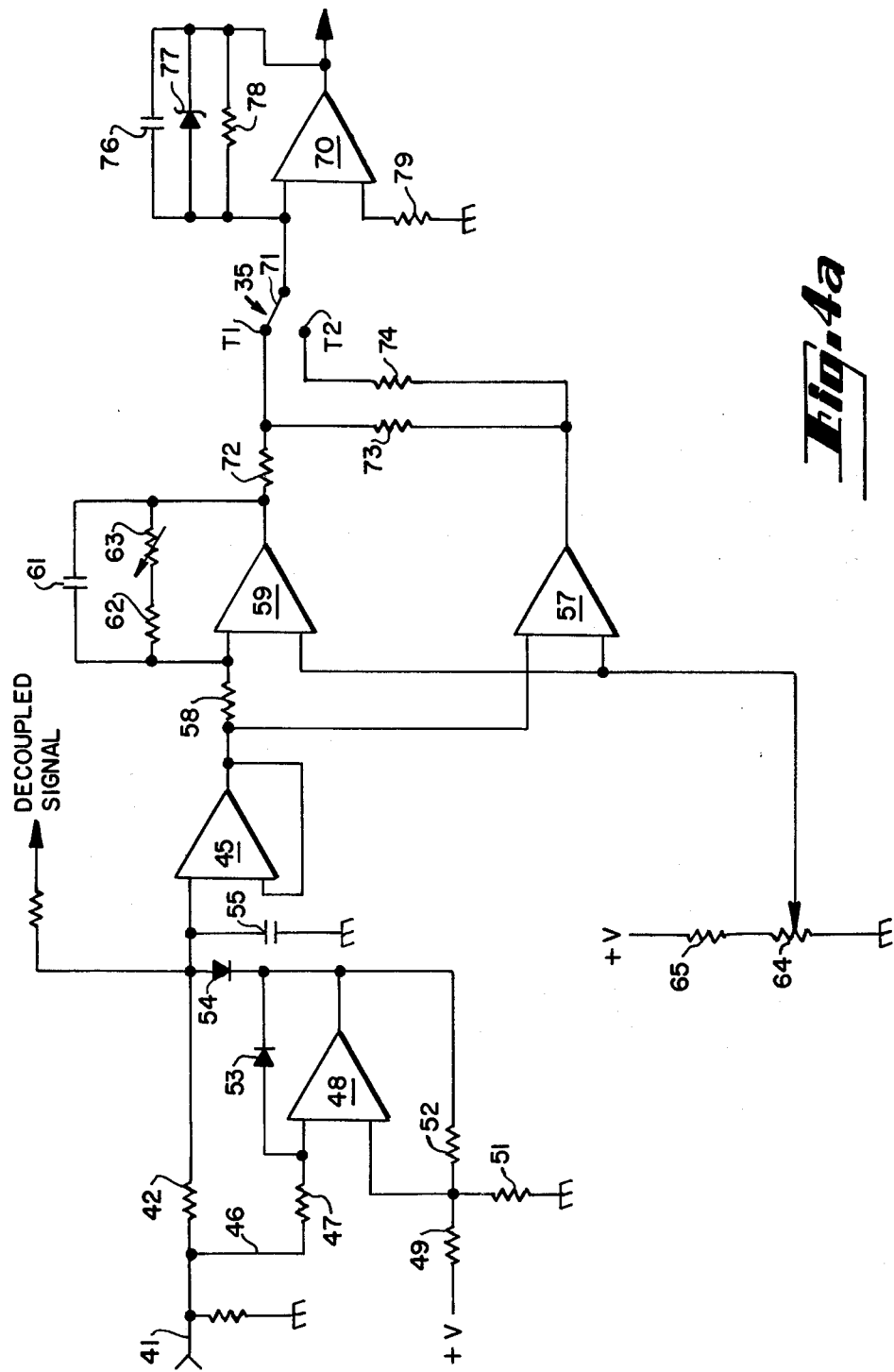
FIGS. 4a and 4b are schematic illustration of the tone generator of the invention.
Figure 4B:
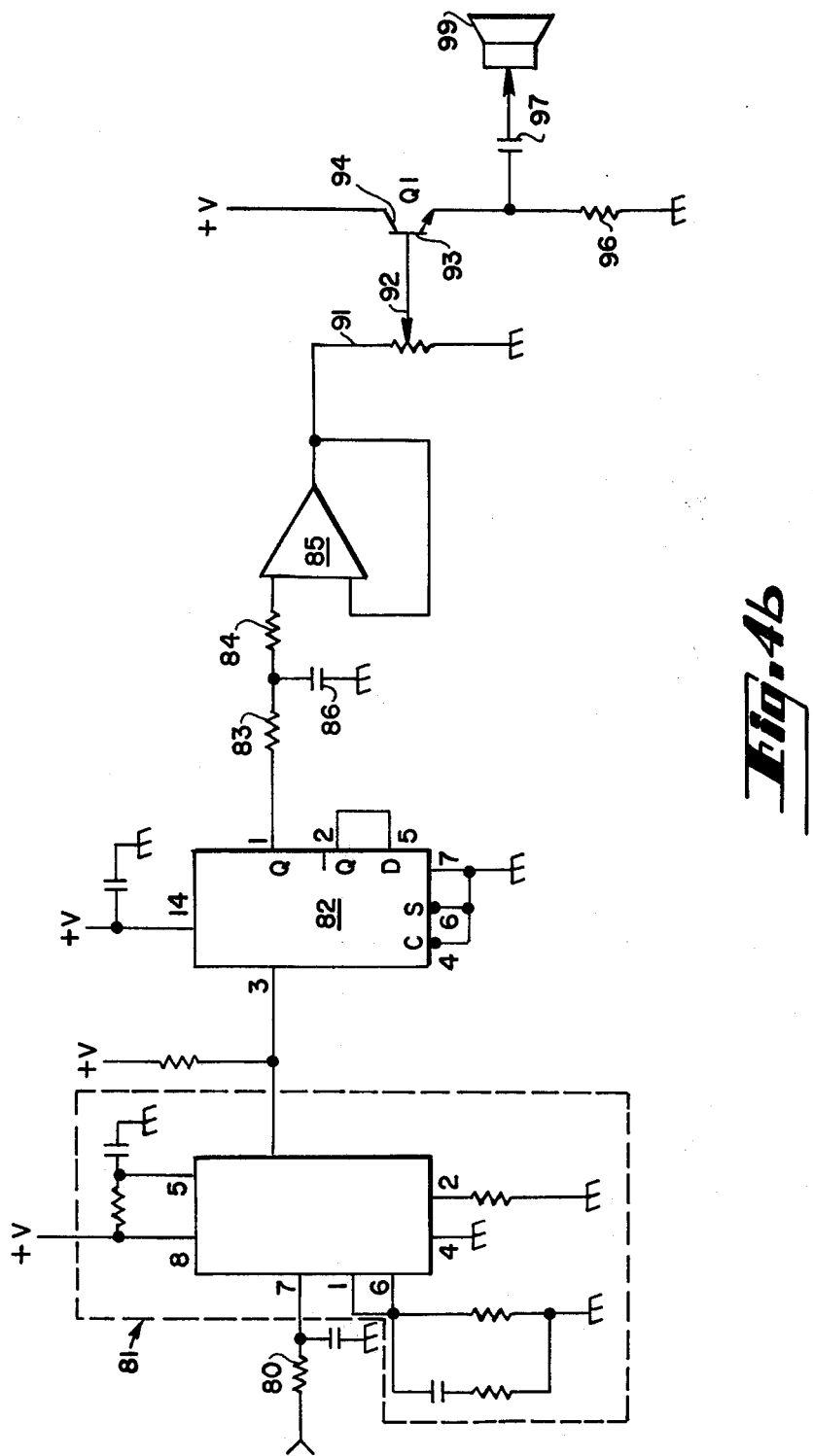

A detailed schematic of the tone generator is provided in FIGS. 4a and 4b. As will be seen therein, the data input signal, representing the transducer output signal from the signal conditioner 23 is coupled by means of a conductor 41 and resistor 42 to the inverting input terminal of a differential amplifier 45 and by a conductor 46 and resistor 46 to the inverting input terminal of a differential amplifier 48. The amplifier 48 is a comparator which measures the input signal and also serves a clamping function hereinafter described.

As will be seen, the noninverting input terminal of amplifier 48 is coupled to the 12 V power supply through a resistance 49 and to ground through a resistance 51. The amplifier output is fed back to its noninverting input terminal through a resistance 52. It is also connected to the cathode of a diode 53 which connects to its own inverting input terminal and also in the cathode of a diode 54 which connects to the inverting input of the amplifier 45.

The comparator amplifier 48 measures the input signals, and signals which do not exceed approximately 1.2 volts have no effect. If the input signal should exceed 1.2 volts, however, the comparator clamps the input to the rest of the circuit of about 1 volt.

The differential amplifier 45 acts as a buffer amplifier and voltage amplifier. Its inverting input is coupled to ground through a capacitor 55 and its output terminal is directly coupled to its noninverting input. In operation, amplifier 45 buffers the signal and feeds its output to the inverting terminals of a pair of differential amplifiers 57 and 59. Its output terminal is coupled through a resistance 58 to the inverting input of amplifier 59. If desired, the signal may also be taken off the inverting terminal of amplifier 45 and used for external monitoring, or the like.

The amplifier 59 is an inverting amplifier with a variable gain and a lowpass filter transfer function provided by a feedback network which couples its output with its inverting input. The feedback network is comprised off a capacitance 61 in parallel with a series-connected pair of resistors—a resistance 62 and a variable resistance 63 for providing variable gain. The other input to the two differential amplifiers 57 and 59 is from the movable contact on an offset level control potentiometer 64 which is coupled to their respective noninverting input terminals. The potentiometer 64 is connected at one side to ground and at its other side to the power supply through a resistance 65.

In operation, the outputs of amplifiers 59 and 57 are negative only when the input data signal is larger than the offset level control which provides the threshold to be exceeded if any audible tone is to be generated.

The output of both amplifiers 59, 57 is selectively coupled through a switch 35 to the inverting input of an operational amplifier 70 when the switch arm 71 is closed in contact with the switch contact T1 as shown in the drawing. The output of amplifier 59 connected with the switch contact T1 through the resistance 72, and the output of amplifier 57 connects with contact T1 through a resistance 73. However, the output of the comparator amplifier 57 is also coupled through a resistance 74 to the other contact T2 of the switch 35, whereby the switch 35 can be used to select the desired mode of operation for the tone generator. The constant single frequency tone, or "chirp" feature, is selected through the switch 35 by choosing the output of the comparator amplifier 57 only. The feedback scan mode, which provides for a signal whose frequency is variable in correspondence with variations in the probe coil impedance as effected by the degree of object displacement or the magnitude and direction of discontinuities therein, is selected by choosing the combined signal from the amplifiers with the switch arm moved to the contact T1.

It is to be noted that so long as the input signal is less than the offset level, the outputs of the comparator 57 is high. However, when the offset level is exceeded, its output goes low. On the other hand, the output of the amplifier 59 varies linearly using the offset level value as the voltage point where the output changes from plus to negative voltage.

It is to be noted that the resistors 73, 74 apportion different portions of the comparator 57 output to the operational amplifier 70 with representative values of 100K ohms and 34K ohms, respectively. In the "chirp" mode, wherein only the comparator output is selected, the resistance 74 allows a relatively large portion of the comparator output to pass to the rest of the circuit for producing a single medium frequency tone.

In the analog feedback scan mode, the output of inverting amplifier 59 is summed together with a relatively small portion of the output of comparator 57. This feature produces a small step function in the tone generated so that for small differences in the input signal, minus the offset control voltage, a low tone is generated. This low tone varies linearly as the input to the inverting amplifier 59 increases.

The operational amplifier 70, which has a low pass transfer function, is provided with a feedback network which feeds its output to its inverting input terminal. The feedback network is comprised of a capacitor 76, a Zener diode 77 which is cathode-connected to the output, and a resistor 78, all in separate parallel branches forming a three-branch parallel network. The noninverting terminal of amplifier 70 is coupled to ground through a resistance 79.

In the feedback scan mode, the amplifier 70 sums the outputs of amplifiers 59 and 57 and performs a negative amplification of the signal. The output is clamped so that it varies only between zero volts and the Zener voltage of about 6.8 volts. Since the gain is −1, the input signal variations are thus limited to the range of 0 to −6.8 volts. Any signal outside this range is clamped by the circuit.

The output of amplifier 70 is connected through a resistance 80 to the input terminal 7 of a voltage-to-frequency converter 81, such as an IC 4-LM 331, which converts an input signal in the range between 0 and 10 volts into a nonsymmetric square wave signal with a frequency which varies linearly between 0 and about 15 kHz.

The converter output is coupled to input terminal 3 of a C MOS D-Flip Flop 82, such as an IC5-CD 4013, which divides the frequency by two and produces a symmetric square wave. This output-from-output terminal 1 is filtered and coupled to the noninverting terminal of an operational amplifier 85 by a T-section filter comprised of the series resistances 83, 84 whose junction is coupled to ground through a capacitor 86. The filter serves to produce a smoother sinusoidal signal and the amplifier 85 buffers the smoothed signal. The output of amplifier 85, which its coupled to is inverting input terminal, is also coupled to one end of a variable resistor or potentiometer 91, the other end of which connects to ground.

Volume control is provided by means of the variable arm 92 which controls the input fo the base 93 of a voltage follower transistor Q1, the collector 94 of which is coupled to the power supply voltage and whose emitter 95 is connected to ground through a resistance 96. The transistor Q1 amplifies the signal current, and its output signal is capacitively coupled through a capacitor 97 to the speaker 99.

It will therefore be apparent that a unique inspection tool is disclosed herein which is particularly suited for nondestructive testing and displacement measurements of metal objects in remote locations and locations for which accessibility is very difficult. The diameter of the flexible insertion tube will, in most instances, be the determining factor in what locations the tool can be used. Since this tube, which includes the fiberoptics and the coil cable, can be made very small and of considerable length (10 feet, or more) it is obvious that the tool can be used in very many places where eddy current testing has heretofore not been feasible.

The tool of this invention speeds gauging and precision measurements by eliminating errors caused by "feel". In this respect, the fiberoptics is particularly helpful. The "chirp" control, which can be used initially when looking for cracks or subsurface inclusions in a target area, is particularly valuable for crack tracing.

The feedback scan control is of most value after the crack has been detected. It provides the operator with a variable audio frequency which can be converted to a "mental map" of the target topography. Accordingly, it allows "audio-optic" analysis of the suspect area without the operator losing eye contact with the fiberoptic scope. In applications for precision displacement (proximity) measurements of such objects as shafts, disks, and the like, the feedback scan control can provide audible information signals as to the degree of displacement.

The sensing tool, when used in displacement measurement applications, is preferably designed to provide an offset between the flat face 11a of the sensor coil and the start of the measuring range as the zero point to provide clearane for a moving target and to avoid contact pressure errors. This offset, preferably 10% of the measuring range, is achieved by placing the face of the coil against a test object and backing away the determined distance. For crack detection, the initial range set up should be 0 to 0.01 inches with zero defined as "the sensor being in contact with the target."

For highly curved targets, improved linearity and stability over the full range may be obtained by reducing the offset voltage; whereas for flat targets, better "close in" linearity may be obtained by increasing the offset.

It is also to be understood that while the eddy current sensor described uses an impedance bridge circuit where its unbalance is reflective of coil impedance changes induced by eddy currents, other test coil circuits such as resonant-circuit types and feedback oscillators affected by coil impedance changes would also be suitable.

The foregoing description of a preferred embodiment of the invention has been presented for purposes of illustration and description. It is not intended to be exhaustive or to limit the invention to the precise form disclosed; and, obviously, many modifications and variations are possible in light of the above teaching. For example, in the feedback scan mode, the audio signal frequency may be made to vary in accord with any of a variety of functions dependent on the transducer input signal. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An eddy current inspection tool for nondestructive testing and detection of discontinuities in metal objects, said tool comprising:

an eddy current sensing coil;

means for activating said coil with a high-frequency signal whereby said coil is adapted to induce eddy currents in objects positioned within the pulsating magnetic field of said coil;

circuit means responsive to impedance changes produced in said coil by the eddy currents induced in the test object, to produce a voltage output data signal which is proportional to the distance between said coil and the test object; and audio signalling means, operable in at least two modes and responsive to said voltage output data signal, for audibly signalling the detection of a discontinuity in the test object, which audio signalling means includes a mode select switch which is selectively operable in a first mode to route said voltage output data signal through means responsive to said voltage output data signal for generating a constant single frequency tone indicating detection of a discontinuity in said test object, and which mode select switch is selectively operable in a second mode to route said voltage output data signal through means responsive to said voltage output data signal for generating from a tone generator means a signal tone whose frequency is proportional to the voltage output data signal whereby said signal tone is indicative of the magnitude of the discontinuity in inspection applications or of the degree of displacement of the test object in displacement measurement applications.

2. An eddy current inspection tool for nondestructive testing and inspection of metal objects, said tool comprising:

a miniaturized test coil;

means for activating said coil with a high frequency electrical signal, whereby said coil is adapted to produce eddy currents in metal objects positioned within the pulsating magnetic field of said coil, said means including a coaxial cable electrically coupling said test coil to said activating means, with said coil being located at the free end of the cable and having a diameter substantially equal to the diameter of said cable, and of a size whereby said coil and coaxial cable can be slideably extended through the utility channel of a fiber optic scope;

circuit means which include said test coil, which is electrically connected in series to an impedance bridge means, which is in turn electrically connected in series of a signal conditioner means, said circuit means being responsive to impedance changes produced in said coil by eddy current induced in the test objects, to produce as an output from said signal conditioner means a voltage output data signal which is proportional to said impedance change; and audio signalling means responsive to said voltage output data signal, for audibly signalling the detection of a discontinuity in the test object, said audio signalling means including a tone generator means for producing the audible signal, a comparator amplifier means electrically connected to said tone generator and which in response to said voltage output data signal produces as an output a constant frequency signal, and an amplifier means electrically connected to said tone generator means and which in response to said voltage output data signal produces as an output a variable frequency signal; and a mode select switch, electrically connected to said audio signalling means to selectively route said constant and variable frequency signals, wherein said mode select switch is selectively operable in a first mode (the "chirp mode") to route said constant frequency signal through means responsive to said constant frequency signal for generating a constant single frequency tone for indicating detection of a discontinuity in said test object or its displacement, and wherein said mode select switch is selectively operable in a second mode (the "feedback scan mode") to combine and route said constant and variable frequency signals emerging from said comparator amplifier means and said amplifier means to means responsive to said frequency signals for generating a signal tone whose frequency is proportional to the voltage of the voltage output data signal.

3. An eddy current sensing tool as described in claim 2, wherein said audio signalling means is provided with a predetermined threshold voltage such that, in either mode of operation said audio signalling means is responsive to said voltage output data signal only when said voltge output data signal exceeds said predetermined threshold voltage, and the frequency of the audible tone generated by said audio signalling means in the second mode (the "feedback scan mode") is proportional to the difference between said voltage output data signal voltage and said threshold voltage.

* * * * *